(12) United States Patent
Balzano

(10) Patent No.: US 7,862,877 B2
(45) Date of Patent: Jan. 4, 2011

(54) SANITARY WRAP

(75) Inventor: Alfiero Balzano, Garden Grove, CA (US)

(73) Assignee: Basic Electronics, Inc., Garden Grove, CA (US)

( * ) Notice: Subject to any disclaimer, the term of this patent is extended or adjusted under 35 U.S.C. 154(b) by 590 days.

(21) Appl. No.: 11/986,085

(22) Filed: Nov. 20, 2007

(65) Prior Publication Data

US 2009/0130005 A1    May 21, 2009

(51) Int. Cl.
*A61L 2/16* (2006.01)
*B32B 1/06* (2006.01)
*B32B 1/04* (2006.01)

(52) U.S. Cl. .............. 428/76; 428/72; 428/90; 428/192; 428/193; 428/198; 428/343; 428/354; 422/292; 422/294

(58) Field of Classification Search .......... 428/68, 428/72, 76, 115, 192, 193, 194, 195.1, 196, 428/198, 200, 201, 156, 157, 172, 343, 351, 428/354, 90, 95; 422/292, 294, 295, 296, 422/297, 300
See application file for complete search history.

(56) References Cited

U.S. PATENT DOCUMENTS

| | | | | |
|---|---|---|---|---|
| 4,765,478 A * | 8/1988 | Bringloe | .............. | 206/440 |
| 5,391,420 A * | 2/1995 | Bootman et al. | ......... | 206/213.1 |
| 6,019,997 A * | 2/2000 | Scholz et al. | .............. | 424/449 |
| 6,083,584 A * | 7/2000 | Smith et al. | .............. | 428/35.2 |
| 6,245,693 B1 * | 6/2001 | Gagliardi et al. | .......... | 442/76 |
| 6,863,960 B2 * | 3/2005 | Curro et al. | .............. | 428/198 |
| 7,132,151 B2 * | 11/2006 | Rasmussen | .............. | 428/182 |
| D534,002 S * | 12/2006 | Butterbaugh et al. | ......... | D5/53 |
| 7,669,736 B2 * | 3/2010 | Harper | .............. | 222/105 |
| 7,690,050 B2 * | 4/2010 | Stockhamer | .............. | 2/69 |
| 7,722,589 B2 * | 5/2010 | Fitts, Jr. et al. | ......... | 604/385.22 |
| 2002/0022427 A1 * | 2/2002 | Curro et al. | .............. | 442/373 |
| 2002/0102392 A1 * | 8/2002 | Fish et al. | .............. | 428/198 |
| 2006/0057369 A1 * | 3/2006 | Hilfenhaus et al. | ......... | 428/343 |
| 2006/0078484 A1 * | 4/2006 | Greep | .............. | 422/300 |
| 2006/0241541 A1 * | 10/2006 | Ravikumar | .............. | 602/46 |
| 2006/0283725 A1 * | 12/2006 | Harper | .............. | 206/210 |
| 2007/0045133 A1 * | 3/2007 | Harper | .............. | 206/210 |
| 2007/0045340 A1 * | 3/2007 | Harper | .............. | 222/105 |
| 2007/0049894 A1 * | 3/2007 | Fitts et al. | .............. | 604/385.22 |
| 2008/0110773 A1 * | 5/2008 | Greep | .............. | 206/205 |
| 2008/0319362 A1 * | 12/2008 | Joseph | .............. | 602/7 |
| 2009/0099531 A1 * | 4/2009 | Griesbach, III | .............. | 604/265 |
| 2009/0099532 A1 * | 4/2009 | Cuevas et al. | .............. | 604/265 |
| 2009/0130005 A1 * | 5/2009 | Balzano | .............. | 422/292 |
| 2009/0155328 A1 * | 6/2009 | Lee | .............. | 424/405 |
| 2010/0037828 A1 * | 2/2010 | Loizides | .............. | 119/161 |
| 2010/0112036 A1 * | 5/2010 | Zhang et al. | .............. | 424/443 |

* cited by examiner

*Primary Examiner*—Cheryl Juska
(74) *Attorney, Agent, or Firm*—Stetina Brunda Garred & Brucker

(57) ABSTRACT

A sanitary article is provided for reducing the spread of contamination between a user and an object. The article comprises a permeable layer, an impermeable layer, and an antibacterial gel interposed between the permeable layer and the impermeable layer. The permeable and impermeable layers may be sealed to each other to restrict the movement of the gel and to make the article unitary. The gel may at least partially diffuse through the permeable layer upon the user contacting the permeable layer while the impermeable layer impeded diffusion of the gel toward the object upon the object contacting the impermeable layer.

18 Claims, 2 Drawing Sheets

SANITARY WRAP

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates generally to hygienic devices, and more specifically, to a uniquely configured sanitary wrap article using permeable and impermeable layers of material that envelop a layer of anti-bacterial gel to diffuse the gel to a user upon contacting the permeable layer without diffusing the gel to an object held against the impermeable layer, thus reducing the spread of contamination between the user and the object.

In recent years, there has been an increasing concern for improving individual cleanliness, and in particular, to protect an individual against common germs and/or other impurities that are located in public places. For example, people often carry sanitizing anti-bacterial gels in their backpacks or purses. After passing through a public place, which often requires the opening of doors, or after handling publicly-used items, people often wash their hands or use the aforementioned anti-bacterial gel. It is apparent that many individuals in society today are becoming increasingly sensitive to the presence of germs on commonly touched items such as door panels, doorknobs, handles, bathroom fixtures such as toilets, sinks, and urinals, etc. In response to these concerns, many devices and methods have been developed that are intended to facilitate the washing or cleansing of hands after the hands have been exposed to publicly touched items.

As mentioned, one of the unique solutions to the problem of contamination has been the use of anti-bacterial gels. Although these gels may be conveniently packaged in small portable containers, people frequently forget to carry the gels, or simply do not have the patience to use the gel after every time they open a door or are otherwise subject to contaminating germs. The use of gels, while done in various situations, may often be a cumbersome process that requires an individual to free both hands so that they can rub the gel thoroughly over both hands and between their fingers. Additionally, although the use of anti-bacterial gels may be helpful on an individual basis, the majority of the public does not commonly use anti-bacterial gels and therefore is subject to picking up contaminating germs from public places.

More traditional means of avoiding contamination include frequent cleaning of the contaminated structures. As is well known, there are a variety of cleaning solutions that are targeted to killing germs and disinfecting commonly used surfaces. These types of disinfectants most commonly are provided in liquid form in spray bottles, and may be applied by simply spraying the disinfectant onto the contaminated surface and wiping off the residue with a clean towel. Although this method is perhaps the most common and widely used method to clean contaminated surfaces, the actual cleaning of such surfaces typically occurs only periodically, and frequently less than once per day in most public places. Therefore, due to the low frequency of the cleaning, people are often subjected to contaminated surfaces throughout much of the day.

Therefore, there is a need in the art for an article useful to maintain public surfaces clean from germs and bacteria. Additionally, there is a need in the art for an article that may be utilized by every individual who encounters a given public surface, such as a doorknob, a door panel, or other hand activated public instruments, such as those found in a restroom. Further, there is a need in the art for an article that may be disposed on the public surface such that each person contacting the public surface may be able to actuate the function of the surface while simultaneously cleaning their hands: Finally, there is a need in the art for an article that is inexpensive, durable, and may be placed on a variety of public surfaces and be securably mounted thereon, withstanding the rigors of use related to the public surface.

BRIEF SUMMARY

In order to address many of the above-mentioned concerns, and for other novel purposes, a sanitary article is provided for reducing the spread of contamination between a user and an object. The sanitary article may be used in a variety of public or private locations, as well as used for handling food, as will be explained below. The novel configuration of the article tends to prevent the spread of contamination from publicly-handled equipment to the user or from the user to food handled by the user.

According to an embodiment of the present invention, the article comprises a permeable layer, an impermeable layer, and an anti-bacterial gel interposed between the permeable layer and the impermeable layer. The permeable layer of material defines a first fringe area. The impermeable layer of material defines a second fringe area. The impermeable layer is sealed to the permeable layer along a continuous seal substantially within the first and second fringe areas of the respective ones of the permeable and impermeable layers. The anti-bacterial gel is interposed between the permeable layer and the impermeable layer. The gel is substantially laterally bounded by the seal between the permeable and impermeable layers. The gel may at least partially diffuse through the permeable layer upon user contact therewith to be imparted to the user. However, the gel is not diffusible through the impermeable layer toward the object upon the object contacting the impermeable layer.

According to another embodiment of the present invention, the sanitary article comprises a permeable layer, an impermeable layer, and an anti-bacterial gel interposed between the permeable layer and the impermeable layer. The permeable layer of material defines first interior and first exterior surfaces, as well as a first fringe area. The impermeable layer of material defines second interior and second exterior surfaces, as well as a second fringe area. The impermeable layer is sealed to the permeable layer along a continuous heat pressed seal substantially within the first and second fringe areas of the respective ones of the permeable and impermeable layers. The anti-bacterial gel is interposed between the permeable layer and the impermeable layer. The gel is substantially laterally bounded by the seal between the permeable and impermeable layers. Further, the gel may at least partially diffuse through the permeable layer upon the user contacting the first exterior surface thereof to be imparted to the user. However, the gel is not diffusible through the impermeable layer toward the object upon the object contacting the second exterior surface of the impermeable layer.

In addition, the permeable layer may also be sealed to the impermeable layer along a plurality of transverse seal lines. The transverse seal lines may be formed within the first and second fringe areas of the respective ones of the permeable and impermeable layers. According to another aspect of the present invention, the second exterior surface may include an adhesive. Thus, the article may be adhesively attached to any variety of surfaces.

According to yet another embodiment of the present invention, the sanitary article may comprise a permeable layer of material and an impermeable layer of material. The permeable layer of material defines first interior and first exterior surfaces, as well as a first fringe area. The permeable layer is impregnated with an anti-bacterial gel. The gel is imparted to a user upon the user contacting the permeable layer. The impermeable layer of material defines second interior and second exterior surfaces, as well as a second fringe area. The impermeable layer is sealed to the permeable layer along a continuous seal substantially within the first and second fringe areas of the respective ones of the permeable and impermeable layers. The impermeable layer impedes the diffusion of the gel toward the object upon the object contacting the second exterior surface of the impermeable layer.

According to an aspect of the present invention, the seal between the permeable and impermeable layers may be a heat pressed seal. Additionally, the anti-bacterial gel may be impregnated into the permeable layer. Further, the permeable layer may be fabricated from a flocked fabric. The impermeable layer may be fabricated from a plastic material.

Although the article may be variously configured, it is contemplated that the permeable layer and the impermeable layer may each define a rectangular perimeter, and that the rectangular perimeters of the respective ones of the permeable and impermeable layers may be aligned.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
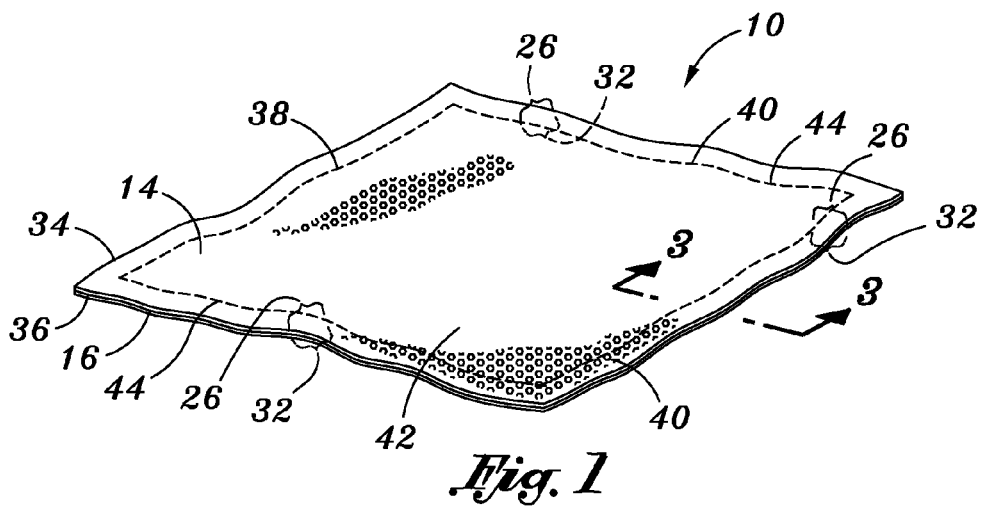
FIG. 1 is a perspective view of an exemplary embodiment of a sanitary article for reducing the spread of contamination between a user and an object.

Referring now to the drawings wherein the showings are for purposes of illustrating preferred embodiments of the present invention and not for purposes of limiting the same, FIG. 1 illustrates an exemplary embodiment of a sanitary article 10 for reducing the spread of contamination between a user and an object 12. The sanitary article 10 may be used in a variety of public or private locations, as well as used for handling food. It is contemplated that the article 10 may be used as a protective layer between the user and the object 12; this may include allowing the user to handle food without washing his hands or handling publicly-touched hardware (such as in restrooms or doors) without being exposed to germs. Thus, the applications for the article 10 are diverse and include use for handling surfaces that are exposed to germs and bacteria, handling sensitive materials, and handling foods, just to name a few. The novel configuration of the article 10 tends to prevent the spread of contamination to or from the user, and presents a timely solution to various contamination issues now facing society.

Figure 2:
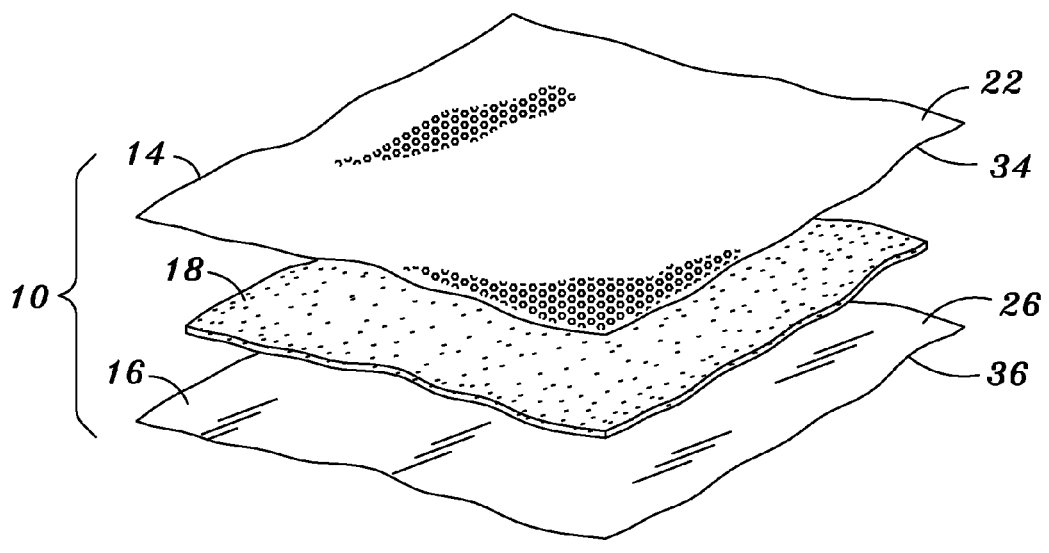
FIG. 2 is an exploded perspective view of the sanitary article including a permeable layer, an impermeable layer, and anti-bacterial gel interposed therebetween according to an embodiment of the present invention.
Figure 3:
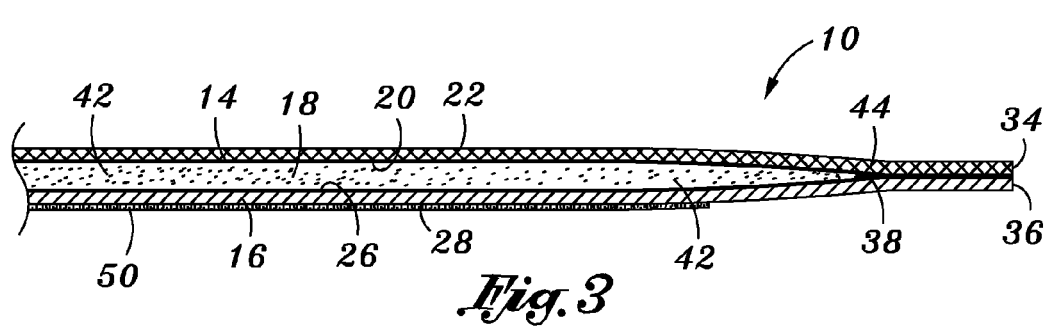
FIG. 3 is a cross sectional view of the sanitary article of FIG. 1 illustrating a pouch formed by the permeable and impermeable layers wherein the gel is disposed, and also illustrating a seal between the permeable and impermeable layers.

According to an embodiment of the present invention shown in FIGS. 1-3, the article 10 comprises a permeable layer 14, an impermeable layer 16, and an anti-bacterial gel 18 interposed between the permeable layer 14 and the impermeable layer 16. The permeable layer 14 of material defines first interior and first exterior surfaces 20, 22, as shown in FIG. 1. The permeable layer 14 also defines a first fringe area 24. Additionally, the impermeable layer 16 of material defines second interior and second exterior surfaces 26, 28, as well as a second fringe area 32. The gel 18 may at least partially diffuse through the permeable layer 14 upon the user contacting the first exterior surface 22 thereof to be imparted to the user. However, the gel 18 is not diffusible through the impermeable layer 16 toward the object 12 upon the object 12 contacting the second exterior surface 28 of the impermeable layer 16.

The permeable layer 14 of material may be made of a variety of materials. Such materials are preferably semi-porous and allow the passage of the gel 18 through the material. It is contemplated that the permeable layer 14 may be non-resilient and plastically-deformable; however, the permeable layer 14 is preferably made of a porous material, such as flocked fabric, which is resilient (i.e. returns to a given shape). Additionally, the permeable layer 14 should preferably be fabricated of a material that is soft to touch. Further, the permeable layer 14 should preferably be fabricated of a material that is durable and can withstand deformation and stresses without tearing and without unraveling.

As shown in FIG. 2, the permeable layer 14 may define a first perimeter 34 and the impermeable layer 16 may define a second perimeter 36. As illustrated, the first and second perimeters 34, 36 may be configured as rectangles. However, the shape and size of the permeable and impermeable layers 14, 16 may be modified as required by a particular application. The first and second perimeters 34, 36 may be shaped as circles, squares, or oblong rectangles depending on the intended use of the article 10. Indeed, as shown in FIG. 1, the shape and size of the permeable layer 14 may generally match the shape and size of the impermeable layer 16 so that when the permeable and impermeable layers 14, 16 are placed together, they combine to form a common perimeter. Thus, the first and second perimeters 34, 36 (illustrated as rectangular in FIGS. 1-2) of the respective ones of the permeable and impermeable layers 14, 16 should preferably be aligned upon assembly.

Figure 5:
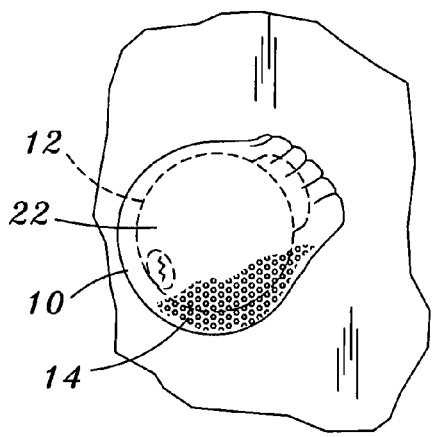
FIG. 5 is a perspective view of the sanitary article being attached to a knob of a door.
Figure 6:
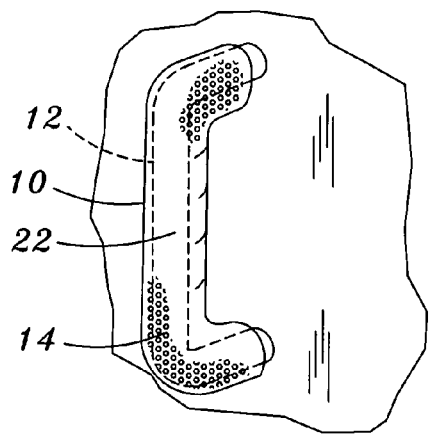
FIG. 6 is a perspective view of the sanitary article being attached to a handle of a door.
Figure 7:
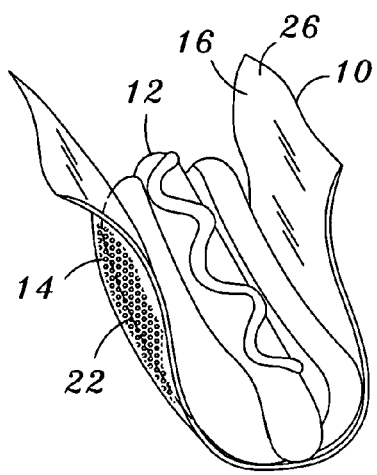
FIG. 7 is a perspective view of the sanitary being wrapped around the object, illustrated as being a hot dog.
Figure 8:
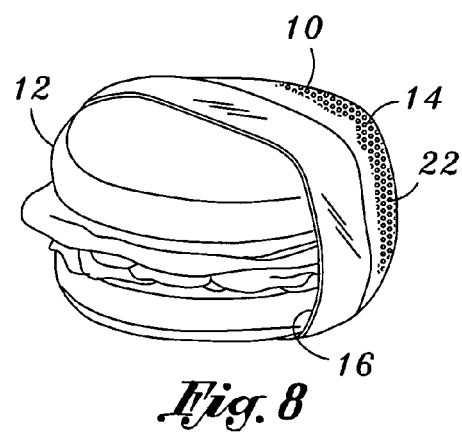
FIG. 8 is a perspective view of the sanitary being wrapped around the object, illustrated as being a hamburger.

The impermeable layer 16 is preferably made of a non-porous material, which thus enables the impermeable layer 16 to block the passage of the gel 18 therethrough. The impermeable layer 16 may be made of plastic. The impermeable layer 16 may also be fabricated from a material that is plastically deformable, thus being non-resilient and conformal to the object 12 to which it is attached or around which it is wrapped. For example, a plastically deformable impermeable layer 16 may be useful in securing the article 10 to a variety of objects 12, such as doorknobs (illustrated in FIG. 5), door handles (illustrated in FIG. 6), and other gripping surfaces. Alternatively, impermeable layer 16 may include an adhesive 50 formed on second exterior surface 28 (shown at FIG. 3), to allow the article 10 to be adhesively attached to a variety of surfaces. Further, the impermeable layer 16 should be fabricated from a material to which humans may be exposed without risk. In this regard, preferred embodiments of the article 10 may be used for food handling, wherein the object is a hot dog (illustrated in FIG. 7) or a hamburger (illustrated in FIG. 8). Thus, the impermeable layer 16, and indeed, the entire article 10, should be made of a material that is safe for food handling.

As mentioned above, the permeable layer 14 is preferably made of a resilient material, therefore, in such applications requiring that the article 10 be plastically deformable, the non-resilience of the impermeable layer 16 should be sufficient to overcome the resilience of the permeable layer 14. In order to accomplish this, the physical properties of the materials used and the configuration of the permeable and impermeable layers 14, 16 (including density, composition, thickness, etc.) should be carefully compared and modified as required.

As indicated above, the permeable layer 14 of material defines the first interior and first exterior surfaces 20, 22, as wells as the first fringe area 24. The first fringe area 24 may be defined as the portion of the permeable layer 14 adjacent the first perimeter 34. The first fringe area 24 is preferably less than one inch in width. Similarly, the impermeable layer 16 of material defines the second interior and second exterior surfaces 26, 28, as well as the second fringe area 32. The second fringe area 32 may be similarly defined as the portion of the impermeable layer 16 that is adjacent the second perimeter 36. The second fringe 32 is also preferably less than one inch in width.

Figure 4:
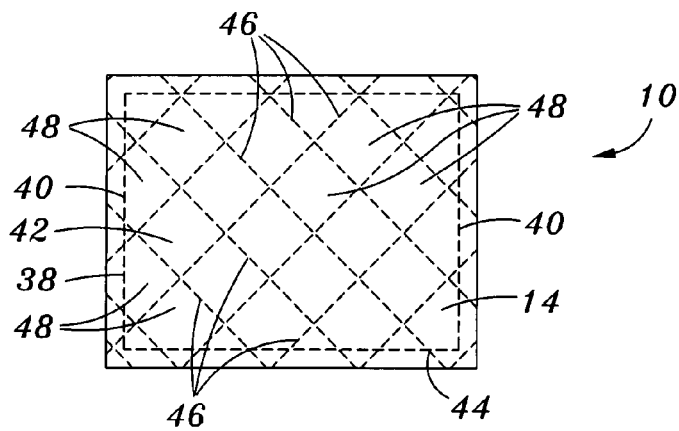
FIG. 4 is a top view of the sanitary article illustrating a seal path of the seal, as well as a plurality of transverse seal lines in accordance with an embodiment of the present invention.

Referring now to FIGS. 1, 3 and 4, the impermeable layer 16 is sealed to the permeable layer 14 along a seal 38 that is disposed inside of the first and second perimeters 34, 36 of the respective ones of the permeable and impermeable layers 14, 16. As shown in FIG. 3, the gel 18 is substantially laterally bounded by the seal 38 between the permeable and impermeable layers 14, 16. In a preferred embodiment shown in FIGS. 1 and 4, the seal 38 is therefore a continuous seal that extends around a seal path 40 disposed within the first and second perimeters 34, 36. Further, the seal 38 may also be disposed substantially within the first and second fringe areas 24, 32 of the respective ones of the permeable and impermeable layers 14, 16.

In accordance with another aspect of the present invention, the article 10 may also include a pouch 42 in which the gel 18 is disposed, as illustrated in FIG. 3. The pouch 42 may be bounded by the permeable layer 14, the impermeable layer 16, and the seal path 40. The pouch 42 may also define a pouch periphery 44, as shown in FIGS. 3 and 4, which may be defined as the boundary within which the gel 18 is disposed, which may be conterminous with the seal path 40 of the seal 38 between the permeable and impermeable layers 14, 16. It is also contemplated that the article 10 may be configured to include multiple pouches 42 with multiple individual pouch peripheries 44.

As will be further discussed below, some embodiments of the present invention provide that the gel 18 may be interposed between the permeable and impermeable layers 14, 16. In such cases, the seal 38 should be continuous to ensure that the gel 18 does not leak outside of the pouch periphery 44. Nevertheless, as may be illustrated with reference to FIG. 3, lateral diffusion of the gel 18 toward the first perimeter 34 of the permeable layer 14 will be possible due to the porous nature of the permeable layer 14. However, significant leakage (not diffusion) is avoided by making the seal 38 a continuous, unbroken seal 38 about the pouch periphery 44. Thus, the gel 18 may be deposited into the pouch 42, with the only mode of exit preferably being diffusion through the permeable layer 14.

The seal 38 may be made using a variety of devices or processed known in the art. However, it is preferred that the seal 38 be made as a heat pressed seal 38. Thus, the materials from which the permeable and impermeable layers 14, 16 are fabricated should be selected in order to ensure that a heat pressed seal 38 (or other type of seal 38 as desired) will be durable to withstand the rigors of use.

In addition, as shown in FIG. 4, the permeable layer 14 may also be sealed to the impermeable layer 16 along a plurality of transverse seal lines 46. The transverse seal lines 46 are where the permeable and impermeable layers 14, 16 are fused together. The transverse seal lines 46 may be formed at any location within the first and second perimeters 34, 36 of the respective ones of the permeable and impermeable layers 14, 16. For example, the transverse seal lines 46 may be within the first and second fringe areas 24, 32 of the respective ones of the permeable and impermeable layers 14, 16. Further, the transverse seal lines 46 may be disposed inside of the first and second fringe areas 24, 32.

The transverse seal lines 46 may be made to tightly bind the permeable layer 14 to the impermeable layer 16, thus making the article 10 unitary, i.e., more similar to a single sheet of material. In addition, the transverse seal lines 46 may also be made on the first and second external surfaces 22, 28 within the pouch perimeter 44 to subdivide the pouch 42 into a plurality of zones 48 (thus subdividing the gel 18 disposed therein into equal portions) so that the gel 18 does not drain to a given zone 48 within the pouch 42. This modification may tend to ensure that preferably equal amounts of gel 18 are available in each zone 48 of the pouch 42. The transverse seal lines 46 may thus dividing the article 10 into the plurality of zones 48 to ensuring even diffusion of the gel 18 throughout the permeable layer 14. Thus, if the article 10 is vertically disposed on the object 12, equal portions of the gel 18 may be restrained to within respective zones 48 of the pouch 42. In such an embodiment, the user may contact any of the zones 48 and be able to have the gel 18 be diffused through the permeable layer 14 to contact the user. Of course, it is contemplated that unequal portions of the gel 18 may be disposed within each of the respective zones 48 of the pouch 42 due to manufacturing limitations. Thus, the transverse seal lines 46 may be discontinuous or dotted, which may tend to maintain a given portion of gel 18 substantially within a given zone 48 while nevertheless allowing minimal passage of the gel 18 to an adjacent zone 48 through discontinuities in the transverse seal lines 46. Further, the transverse seal lines 46 may be oriented orthogonally with respect to the first and second perimeters 34, 36, or transverse thereto. Other designs, such as using circles, waves, or the like, may be developed and implemented within the scope of various embodiments of the present invention.

According to yet another aspect of the present invention, the permeable layer 14 may be impregnated with the antibacterial gel 18. Thus, the gel 18 may easily be imparted to a user upon the user contacting the permeable layer 14 while the impermeable layer 16 of material impedes diffusion of the gel 18 to the object 12. This feature may allow for simple fabrication of the article 10 using only two layers of material and a sealing apparatus. Further, the use of the impregnated permeable layer 14 ensures that equal portions of the gel 18 are disposed on the permeable layer 14. Thus, while such a modification would not require the seal 38 to form a boundary through which the gel 18 cannot diffuse, the seal 38 would still serve to join the permeable layer 14 to the impermeable layer 16. Further, the transverse seal lines 46 may also be used to tightly bind the permeable layer 14 to the impermeable layer 16, thus making the article 10 more similar to a single sheet of material.

The above description is given by way of example, and not limitation. Given the above disclosure, one skilled in the art could devise variations that are within the scope and spirit of the invention disclosed herein, including various ways of manufacturing the article 10 in layerwise fashion, modifying the configuration of the article 10 to correspond to the handling of various objects and/or foods, as well as the use of alternative gels 18. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A sanitary article for reducing the spread of contamination between a user and an object, the article comprising:
   a permeable layer of material defining a first fringe area;
   an impermeable layer of material defining a second fringe area, the impermeable layer being sealed to the permeable layer along a continuous seal substantially within the first and second fringe areas of the respective ones of the permeable and impermeable layers, the impermeable layer further including an adhesive disposed on an exterior surface of the impermeable layer;
   an anti-bacterial gel interposed between the permeable layer and the impermeable layer, the gel being substantially laterally bounded by the seal between the permeable and impermeable layers;
   wherein the gel at least partially diffuses through the permeable layer upon user contact therewith to be imparted to the user, and wherein the gel is not diffusible through the impermeable layer toward the object upon the object contacting the impermeable layer.

2. The article of claim 1 wherein the seal is a heat pressed seal.

3. The article of claim 1 wherein the anti-bacterial gel is impregnated into the permeable layer.

4. The article of claim 1 wherein the permeable layer is fabricated from a flocked fabric.

5. The article of claim 1 wherein the impermeable layer is fabricated from a plastic material.

6. The article of claim 1 wherein the article includes a pouch wherein the gel is disposed, the pouch defining a pouch perimeter, and wherein the permeable layer is sealed to the impermeable layer along a plurality of transverse seal lines disposed within the pouch perimeter, the transverse seal lines dividing the article into a plurality of zones for ensuring even diffusion of the gel throughout the permeable layer.

7. The article of claim 6 wherein each of the plurality of zones includes substantially equal amounts of gel disposed therein.

8. The article of claim 1 wherein the permeable layer defines a rectangular perimeter and the impermeable layer also defines a rectangular perimeter, the rectangular perimeters of the respective ones of the permeable and impermeable layers being aligned.

9. A sanitary article for reducing the spread of contamination between a user and an object, the article comprising:
   a permeable layer of material defining first interior and first exterior surfaces, the permeable layer further defining a first fringe area;
   an impermeable layer of material defining second interior and second exterior surfaces, the impermeable layer further defining a second fringe area, the impermeable layer being sealed to the permeable layer along a continuous heat pressed seal substantially within the first and second fringe areas of the respective ones of the permeable and impermeable layers, the impermeable layer second exterior surface having an adhesive disposed thereon; and
   an anti-bacterial gel interposed between the permeable layer and the impermeable layer, the gel being substantially laterally bounded by the seal between the permeable and impermeable layers;
   wherein the gel at least partially diffuses through the permeable layer upon the user contacting the first exterior surface thereof to be imparted to the user, and wherein the gel is not diffusible through the impermeable layer toward the object upon the object contacting the second exterior surface of the impermeable layer.

10. The article of claim 9 wherein the article includes a pouch wherein the gel is disposed, the pouch defining a pouch perimeter, and wherein the permeable layer is sealed to the impermeable layer along a plurality of transverse seal lines disposed within the pouch perimeter, the transverse seal lines dividing the article into a plurality of zones for ensuring even diffusion of the gel throughout the permeable layer.

11. The article of claim 10 wherein each of the plurality of zones includes substantially equal amounts of gel disposed therein.

12. The article of claim 9 wherein the permeable layer of material is flocked fabric.

13. The article of claim 9 wherein the impermeable layer is fabricated from a plastic material.

14. A sanitary article for reducing the spread of contamination between a user and an object, the article comprising:
   a permeable layer of material defining first interior and first exterior surfaces, the permeable layer further defining a first fringe area, the permeable layer being impregnated with an anti-bacterial gel, the gel being imparted to a user upon the user contacting the permeable layer; and
   a impermeable layer of material defining second interior and second exterior surfaces, the impermeable layer further defining a second fringe area, the impermeable layer being sealed to the permeable layer along a continuous seal substantially within the first and second fringe areas of the respective ones of the permeable and impermeable layers, the impermeable layer impeding the diffusion of the gel toward the object upon the object contacting the second exterior surface of the impermeable layer, the impermeable layer having an adhesive disposed on the second exterior surface thereof.

15. The article of claim 14 wherein the seal is a heat pressed seal.

16. The article of claim 14 wherein the permeable layer of material is flocked fabric.

17. The article of claim 14 further including a plurality of transverse seal lines, the transverse seal lines dividing the article into a plurality of zones for ensuring even diffusion of the gel throughout the permeable layer.

18. The article of claim 17 wherein each of the plurality of zones includes substantially equal amounts of gel disposed therein.

* * * * *